United States Patent
Ishii et al.

(10) Patent No.: US 7,081,551 B2
(45) Date of Patent: *Jul. 25, 2006

(54) OPTICALLY ACTIVE (R)-1-(4-TRIFLUOROMETHYLPHENYL) ETHYLAMINE

(75) Inventors: Akihiro Ishii, Saitama (JP); Manabu Yasumoto, Saitama (JP); Yokusu Kuriyama, Saitama (JP); Masatomi Kanai, Saitama (JP); Kanjin Inomiya, Saitama (JP)

(73) Assignee: Central Glass Co., Ltd., Ube (JP)

( * ) Notice: Subject to any disclaimer, the term of this patent is extended or adjusted under 35 U.S.C. 154(b) by 294 days.

This patent is subject to a terminal disclaimer.

(21) Appl. No.: 10/442,652

(22) Filed: May 21, 2003

(65) Prior Publication Data
US 2004/0024253 A1    Feb. 5, 2004

(30) Foreign Application Priority Data
May 21, 2002    (JP)    ............................. 2002-146983

(51) Int. Cl.
C07C 209/28    (2006.01)
C07C 251/24    (2006.01)
C07C 211/03    (2006.01)

(52) U.S. Cl. ...................... 564/397; 564/272; 564/392
(58) Field of Classification Search ...................... None
See application file for complete search history.

(56) References Cited

U.S. PATENT DOCUMENTS 6,797,842 B1 * 9/2004 Ishii et al. ................... 564/384

2002/0103400 A1    8/2002 Ishii et al.

FOREIGN PATENT DOCUMENTS

| JP | 2002-003453 | 1/2002 |
|---|---|---|
| JP | 2002-030048 | 1/2002 |
| JP | 2002-173472 | 6/2002 |
| JP | 2002-187873 | 7/2002 |
| JP | 2002-255908 | 9/2002 |
| JP | 2002-308836 | 10/2002 |
| WO | WO 00/66558 | 11/2000 |

OTHER PUBLICATIONS

Smith et al., "Optically Active Amines. 31.[1] Spectral Observations on the Substituted Benzene Chromophore[2]", *J. Am. Chem. Soc.*, vol. 105 (1983), pp. 1578-1584.

* cited by examiner

*Primary Examiner*—Brian Davis
(74) *Attorney, Agent, or Firm*—Crowell & Moring LLP

(57) ABSTRACT

Optically active (R)-1-(4-trifluoromethylphenyl)ethylamine is a novel compound as an important intermediate for medicines and agricultural chemicals. This compound can be obtained with high optical purity and high yield by a process including the steps of (a) a dehydrocondensation of 4'-(trifluoromethyl)acetophenone and an optically active (R)-1-phenylethylamine to obtain an optically active imine; (b) asymmetrically reducing the imine into an optically active secondary amine; (c) reacting the amine with an organic acid (phthalic acid or benzenesulfonic acid), thereby obtaining a product that is a phthalate of or benzenesulfonate of the amine; (d) subjecting the product of the step (c) to a hydrogenolysis, thereby obtaining a product that is a phthalate of or benzenesuilfonate of optically active (R)-1-(4-trifluoromethylphenyl)ethylamine; and (e) neutralizing the product of the step (d) into the optically active (R)-1-(4-trifluoromethylphenyl)ethylamine.

18 Claims, No Drawings

OPTICALLY ACTIVE (R)-1-(4-TRIFLUOROMETHYLPHENYL) ETHYLAMINE

BACKGROUND OF THE INVENTION

The present invention relates to optically active (R)-1-(4-trifluoromethylphenyl)ethylamine, which is a novel compound as an important intermediate for medicines and agricultural chemicals.

Optically active 1-(4-trifluoromethylphenyl)ethylamine is an important intermediate for medicines and agricultural chemicals. It corresponds to a partial structure of Sch-350634 as a CCR5 antagonist against Human Immunodeficiency Virus (HIV) (see WO 00/66558). J. Am. Chem. Soc., Vol. 105, pp. 1578–1584 (1983) discloses a process for producing optically active (S)1-(4-trifluoromethylphenyl)ethylamine from its racemic mixture using L-N-acetylleucine as a resolution agent.

SUMMARY OF THE INVENTION

It is an object of the present invention to provide a novel compound of optically active (R)-1-(4-trifluoromethylphenyl)ethylamine, which can be an important intermediate for medicines and agricultural chemicals.

According to the present invention, there is provided optically active (R)-1-(4-trifluoromethylphenyl)ethylamine represented by the formula [1].

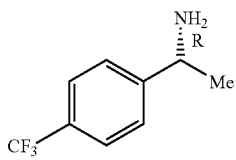

[1]

According to the present invention, the above-mentioned optically active (R)-1-(4-trifluoromethylphenyl)ethylamine can be produced by a process comprising the steps of:

(a) reacting 4'-(trifluoromethyl)acetophenone represented by the formula [8], with optically active (R)-1-phenylethylamine represented by the formula [9], under an acidic condition to generate a dehydrocondensation, thereby obtaining an optically active imine represented by the formula [2];

(b) asymmetrically reducing the optically active imine into an optically active secondary amine represented by the formula [3];

(c) reacting the optically active secondary amine with an organic acid that is phthalic acid or benzenesulfonic acid, thereby obtaining a product that is a phthalate of the optically active secondary amine or a benzenesulfonate of the optically active secondary amine, the phthalate and the benzenesulfonate being respectively represented by the formulas [4] and [5];

(d) subjecting the product of the step (c) to a hydrogenolysis, thereby obtaining a product that is a phthalate of optically active (R)-1-(4-trifluoromethylphenyl)ethylamine or a benzenesulfonate of optically active (R)-1-(4-trifluoromethylphenyl)ethylamine, the phthalate and the benzenesulfonate being respectively represented by the formulas [6] and [7]; and (e) neutralizing the product of the step (d) into the optically active (R)-1-(4-trifluoromethylphenyl)ethylamine.

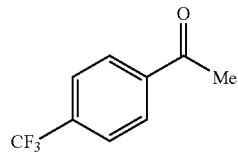

[8]

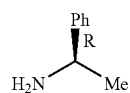

[9]

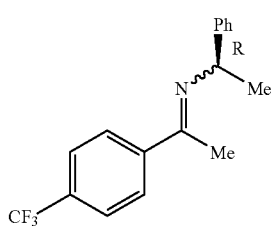

[2]

where a zigzag line in the formula [2] indicates that the optically active imine is in an E configuration or Z configuration,

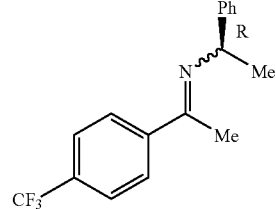

[3]

where * represents an asymmetric carbon, and the optically active secondary amine comprises a first stereoisomer of R configuration and a second stereoisomer of S configuration, the first stereoisomer is in an amount greater than that of the second stereoisomer,

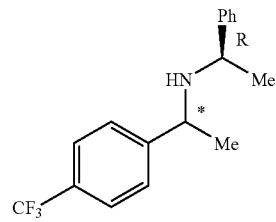

[4]

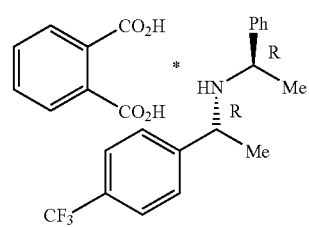

[5]

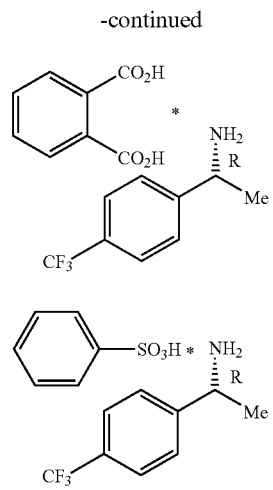

DESCRIPTION OF THE PREFERRED EMBODIMENTS

The above-mentioned process for producing a novel compound of optically active (R)-1-(4-trifluoromethylphenyl) ethylamine is illustrated with the following reaction scheme:

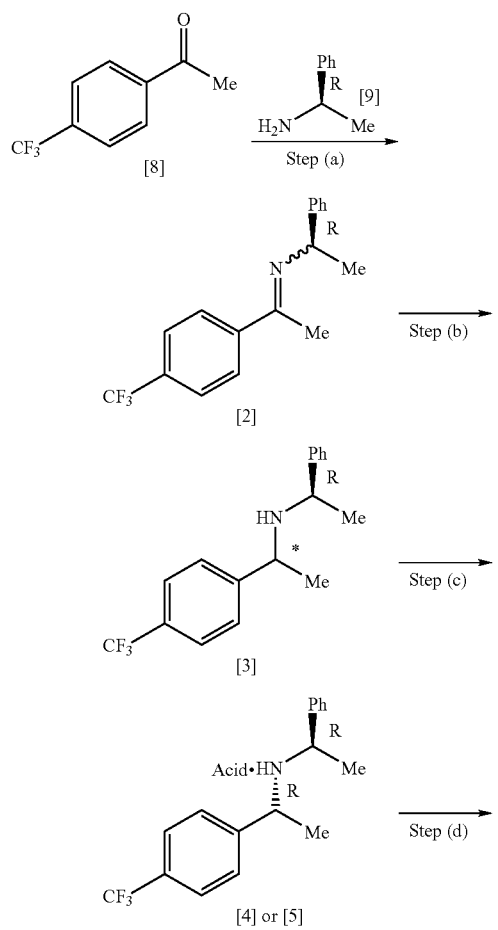

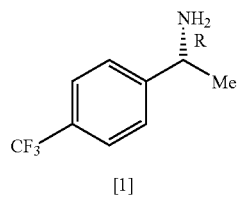

where "Acid" in the formulas [4], [5], [6] or [7] is phthalic acid or benzenesulfonic acid.

The above-mentioned intermediates produced in the process, which are represented by the formulas [2] to [7], are novel compounds, as well as the target product of the process, that is, optically active (R)-1-(4-trifluoromethylphenyl)ethylamine. The process makes it possible to produce optically active (R)-1-(4-trifluoromethylphenyl)ethylamine with high optical purity (e.g., an enantiomeric excess ratio of at least 90% ee) and high yield.

The above-mentioned process for producing optically active (R)-1-(4-trifluoromethylphenyl)ethylamine is described in detail as follows.

The optically active imine represented by the formula [2] (see the above reaction scheme) can efficiently be produced by the step (a), as explained in the following.

In the step (a), optically active (R)-1-phenylethylamine of the formula [9] may have an optical purity of not lower than 98% ee (% ee represents enantiomeric excess ratio).

In the step (a), the amount of optically active (R)-1-phenylethylamine may be at least one mole, preferably 1–10 moles, particularly preferably 1–5 moles, per mol of 4'-(trifluoromethyl) acetophenone of the formula [8].

The step (a) is a dehydrocondensation (i.e., dehydration and condensation) of a ketone represented by the formula [8] and an optically active primary amine represented by the formula [9]. Therefore, the reaction is conducted under an acidic condition, while water as a by-product is removed. It is preferable to conduct the reaction under reflux using a solvent that is immiscible with water, that has a specific gravity lower than that of water, and that forms an azeotropic mixture with water, while water as a by-product is removed by a Dean-Stark trap.

The reaction solvent of the step (a) is not particularly limited, as long as it forms an azeotropic mixture with water. It is preferably an aromatic hydrocarbon such as benzene, toluene, ethylbenzene, xylene, and mesitylene, particularly preferably toluene. These solvents can be used alone or in combination.

In the step (a), the reaction solvent is used in an amount such that the amount of water theoretically produced in the reaction can be separated from the reaction liquid as an azeotropic mixture of water and the reaction solvent. It is, however, possible to extremely lower the amount of the reaction solvent by using a Dean-Stark trap.

It is possible to use an acid catalyst in the step (a) to make an acidic condition. The acid catalyst may be selected from organic acids (e.g., benzenesulfonic acid, p-toluenesulfonic acid, and 10-camphorsulfonic acid) and inorganic acids (e.g., hydrochloric acid, sulfuric acid, phosphoric acid, zinc chloride, and titanium tetrachloride). Of these, p-toluenesulfonic acid, sulfuric acid, and zinc chloride are preferable. In particular, p-toluenesulfonic acid and zinc chloride are more preferable.

The acid catalyst of the step (a) may be in a catalytic amount, preferably 0.001–1 mol, more preferably 0.005–0.5 moles, per mol of the ketone of the formula [8].

The reaction of the step (a) can be conducted at a temperature from the azeotrope temperature, at which an azeotropic mixture of water and the reaction solvent is boiled, to the boiling point of the reaction solvent. It is preferably in the vicinity of the boiling point of the reaction solvent.

It is possible to obtain a crude product of the step (a) by conducting an ordinary post-treatment after the reaction. According to need, the crude product can be subjected to a purification such as the use of activated carbon, distillation, recrystallization, or column chromatography, thereby obtaining the optically active imine of the formula [2] with high purity.

The optically active secondary amine represented by the formula [3] (see the above reaction scheme) can efficiently be produced by the step (b), as explained in the following.

The step (b), that is, an asymmetric reduction of the optically active imine of the formula [2], can proceed well by "hydride reduction".

A hydride reducing agent to be used in the step (b) can be selected from (1) aluminum hydrides such as $(i-Bu)_2AlH$, $(i-Bu)_3Al$, $[2,6-(t-Bu)_2-4-Me-Ph]Al(i-Bu)_2$, $LiAlH_4$, $LiAlH(OMe)_3$, $LiAlH(O-t-Bu)_3$, and $NaAlH_2(OCH_2CH_2OCH_3)_2$; (2) boron hydrides such as diborane, $BH_3.THF$, $BH_3.SMe_2$, $BH_3.NMe_3$, 9-BBN, $NaBH_4$, $NaBH_4$-$CeCl_3$, $LiBH_4$, $Zn(BH_4)_2$, $Ca(BH_4)_2$, $Lin-BuBH_3$, $NaBH(OMe)_3$, $NaBH(OAc)_3$, $NaBH_{13}CN$, $Et_4NBH_4$, $Me_4NBH(OAc)_3$, $(n-Bu)_4NBH_3CN$, $(n-Bu)_4NBH(OAc)_3$, $Li(s-Bu)_3BH$, $K(s-Bu)_3BH$, $LiSia_3BH$, $KSia_3BH$, $LiEt_3BH$, $KPh_3BH$, $(Ph_3P)_2CuBH_4$, $ThxBH_2$, $Sia_2BH$, catecholborane, $IpcBH_2$, and Ipc2BH; and (3) silicon hydrides such as $Et_3SiH$, $PhMe_2SiH$, $Ph_2SiH_2$, and $PhSiH_3$-$Mo(CO)_6$. Of these, preferable examples are $LiAlH_4$, diborane, $NaBH_4$, and $LiBH_4$. In particular, $LiAlH_4$ and $NaBH_4$ are more preferable. It is possible to use a combination of at least one of these hydrides and at least one of various inorganic salts.

In the step (b), the hydride reducing agent may be in an amount of 0.25 moles or greater, preferably 0.25–10 moles, more preferably 0.25–7 moles, per mol of the optically imine of the formula [2].

A reaction solvent used in the step (b) is not particularly limited. Its examples are (1) aliphatic hydrocarbons such as n-pentane, n-hexane, c-hexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; (5) esters such as ethyl acetate and n-butyl acetate; (6) nitrites such as acetonitrile and propionitrile; (7) alcohols such as methanol, ethanol, n-propanol, and i-propanol; and (8) carboxylic acids such as acetic acid, propionic acid, and butyric acid. Of these, preferable examples are diethyl ether, tetrahydrofuran, t-butyl methyl ether, methanol, ethanol, and i-propanol. In particular, tetrahydrofuran, methanol, ethanol, and i-propanol are more preferable. It is possible to use a single solvent or a mixture of at least two of these.

The reaction of the step (b) can be conducted at a temperature of from $-100$ to $+100°$ C., preferably from $-80$ to $+80°$ C., more preferably from $-60$ to $+60°$ C.

It is possible to obtain a crude product of the step (b) by conducting an ordinary post-treatment after the reaction. According to need, the crude product can be subjected to a purification such as the use of activated carbon, distillation, recrystallization, or column chromatography, thereby obtaining the optically active secondary amine of the formula [3] with high purity.

A phthalate of or benzenesulfonate of the optically active secondary amine, which is represented by the formula [4] or [5] (see the above reaction scheme), can efficiently be induced by the step (c).

The step (c) can be conducted by reacting the optically active secondary amine of the formula [3] with an organic acid (i.e., phthalic acid or benzenesulfonic acid), followed by recrystallization with a recrystallization solvent to purify the product of the step (c).

The secondary amine used in the step (c) can have an optical purity of 10% de (% de represents diastereomer excess ratio).

In addition to the above-mentioned phthalic acid (i.e., o-benzenedicarboxylic acid) and benzenesulfonic acid, the organic acid of the step (c) may be selected from (1) aliphatic carboxylic acids such as acetic acid, propionic acid, butyric acid, isobutyric acid, valeric acid, isovaleric acid, hexanoic acid, heptanoic acid, cyclohexanecarboxylic acid, octanoic acid, phenylacetic acid and 3-phenylpropionic acid; (2) haloalkylcarboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid; (3) unsaturated carboxylic acids such as acrylic acid, crotonic acid, citraconic acid, maleic acid, fumaric acid and cis- or trans-cinnamic acid; (4) aromatic carboxylic acids such as benzoic acid, o, m- or p-toluic acid, o-, m- or p-fluorobenzoic acid, o-, m- or p-chlorobenzoic acid, o-, m- or p-bromobenzoic acid, o-, m- or p-iodobenzoic acid, o, m- or p-hydroxybenzoic acid, o-, m- or p-anisic acid, o-, m- or p-aminobenzoic acid, o-, m- or p-nitrobenzoic acid, o-, m- or p-cyanobenzoic acid, m- or p-benzenedicarboxylic acid (isophthalic acid or terephthalic acid), α-, β- or γ-picolinic acid, 2,6-pyridinedicarboxylic acid and 1- or 2-naphthoic acid; (5) sulfonic acids such as methanesulfonic acid, chloromethanesulfonic acid, trifluoromethanesulfonic acid, p-toluenesulfonic acid and p-phenolsulfonic acid; (6) optically active carboxylic acids such as lactic acid, malic acid, tartaric acid, dibenzoyltartaric acid, 2-phenylpropionic acid, mandelic acid, camphoric acid and cis-2-benzamidocyclohexanecarboxylic acid; (7) optically active sulfonic acids such as phenylethanesulfonic acid and 10-camphorsulfonic acid; (8) optically active phosphoric acids such as 2,2'-(1,1'-binaphthyl)phosphoric acid; (9) optically active amino acids such as 4-aminobutyric acid, phenylglycine and aspartic acid; (10) optically active N-acylamino acids such as pyroglutamic acid, N-acetyl-3,5-dibromo-tyrosine, N-acylphenylalanine, N-acyl-aspartic acid, N-acylglutamic acid and N-acylproline (wherein, N-acyl group represents acetyl group, benzyloxycarbonyl group, benzoyl group, benzenesulfonyl group, p-toluenesulfonyl group and the like), and (11) other organic acids such as formic acid, oxalic acid, malonic acid, succinic acid, adipic acid, pimelic acid, cyanoacetic acid, citric acid, glycolic acid, glyoxylic acid, pyruvic acid, levulinic acid, oxaloacetic acid, mercaptoacetic acid, phenoxyacetic acid and picric acid. Although the optically active carboxylic acids, the optically active sulfonic acids, the optically active phosphoric acids, the optically active amino acids or the optically active N-acylamino acids exist in R configuration or in S configuration, their enantiomers may be suitably selected for use. Among these, phthalic acid and benzenesulfonic acid are more preferable, as mentioned hereinbefore. It is naturally possible by the step (c) to obtain a salt of the optically active secondary amine, which is different from the above-mentioned phthalate or benzenesulfonate represented by the formula [4] or [5] by using an organic acid other than phthalic acid or benzenesulfonic acid.

In the step (c), the organic acid may be in an amount of 0.3 moles or greater, preferably 0.3–5 moles, more preferably 0.3–3 moles, per mol of the optically active secondary amine of the formula [3].

The actual operation of the step (c) can suitably be selected in view of the combination of the organic acid and the optically active secondary amine. For example, it is possible to conduct the step (c) by directly adding the optically active secondary amine and an organic acid into a recrystallization solvent, followed by mixing. Alternatively, it is possible to mix a solution of the optically active secondary amine with a solution of the organic acid to conduct the step (c).

The recrystallization solvent of the step (c) is not particularly limited as long as it does not react with the optically active secondary amine, the organic acid, and the salt obtained by the step (c). The recrystallization solvent can suitably be selected in view of, for example, (a) the diastereomer excess ratio prior to purification of the salt using the recrystallization solvent, (b) the diastereomer excess ratio after that, and (c) recovery.

The recrystallization solvent of the step (c) may be selected from (1) aliphatic hydrocarbons such as n-pentane, n-hexane, c-hexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) ketones such as acetone, methyl ethyl ketone, and methyl isobutyl ketone; (6) esters such as ethyl acetate and n-butyl acetate; (7) nitriles such as acetonitrile and propionitrile; (8) alcohols such as methanol, ethanol, n-prop anol, i-propanol, and n-butanol; and (9) water. Of these, preferable examples are n-hexane, n-heptane, toluene, methylene chloride, t-butyl methyl ether, acetone, ethyl acetate, acetonitrile, methanol, ethanol, n-propanol, and i-propanol. It is possible to use a single solvent or a mixture of at least two of these.

The amount of the recrystallization solvent of the step (c) is not particularly limited, as long as the product (salt) of the step (c) is completely or partially dissolved therein under heating. It can suitably be selected in view of, for example, (a) the diastereomer excess ratio prior to purification of the salt using the recrystallization solvent, (b) the diastereomer excess ratio after that, and (c) recovery. For example, the recrystallization solvent may be in an amount of at least 1 part by volume, preferably 1–100 parts by volume, more preferably 1–50 parts by volume, relative to the phthalate of the formula [4] or the benzenesulfonate of the formula [5].

The recrystallization of the step (c) proceeds smoothly and efficiently by adding seed crystals. The seed crystals are in an amount of preferably from 1/10,000 to 1/10 parts by weight, more preferably from 1/1,000 to 1/20 parts by weight, relative to one part by weight of the salt (product) of the step (c) prior to purification.

The temperature for conducting the recrystallization may suitably be selected in view of boiling point and freezing point of the recrystallization solvent. For example, the recrystallization may be conducted by dissolving the salt prior to purification in a recrystallization solvent at a temperature of from room temperature (e.g., 25° C.) to a temperature close to boiling point of the recrystallization solvent and then by precipitating crystals at a temperature of −40 to +80° C.

The precipitated crystals can be recovered by filtration or the like to increase the diastereomer excess ratio of the crystals. With this, it is possible to make the salt (product) of the step (c) have high purity. Its purity can be improved further by repeating the recrystallization operation.

A phthalate of or benzenesulfonate of optically active (R)-1-(4-trifluoromethylphenyl)ethylamine, which is represented by the formula [6] or [7] (see the above reaction scheme), can efficiently be produced by hydrogenolysis of the step (d), as explained in the following.

The hydrogenolysis can proceed well by a catalytic reduction using a transition metal complex as a catalyst. This transition metal complex can be selected from (1) platinum catalysts such as platinum oxide, platinum/active carbon and platinum black; (2) nickel catalysts such as reduced nickel, Raney nickel and platinum-Raney nickel; (3) cobalt catalysts such as Raney cobalt; (4) copper catalysts such as reduced copper and copper-chromium oxide; (5) zinc catalysts such as zinc-chromium oxide; (6) ruthenium catalysts such as ruthenium oxide and ruthenium/active carbon; (7) rhodium catalysts such as rhodium/active carbon, rhodium/alumina and rhodium-platinum oxide; (8) iridium catalysts such as iridium black; (9) rhenium catalysts such as rhenium oxide; and palladium catalysts such as palladium/active carbon, palladium hydroxide, palladium black, palladium/barium sulfate, palladium/strontium carbonate, palladium/calcium carbonate, palladium/calcium carbonate-lead diacetate, palladium/barium sulfate-quinoline, palladium/alumina, palladium sponge, palladium chloride, palladium acetate, palladium acetylacetonate, bis(dibenzylideneacetone)palladium, tetrakis(triphenylphosphine)palladium, dichloro[bis(triphenylphosphine)]palladium, dichloro[bis(diphenylphosphino)methane]palladium, dichloro[bis(diphenylphosphino)ethane]palladium, dichloro[1,3-bis(diphenylphosphino)propane]palladium, dichloro[1,4-bis(diphenylphosphino)butane]palladium, dichloro(1,5-cyclooctadiene)palladium, dichloro[bis(benzonitrile)]palladium, dichloro[bis(acetonitrile)]palladium and [bis(triphenylphosphine)]palladium acetate. Among these, platinum catalysts, rhodium catalysts and palladium catalysts are preferable, and platinum/active carbon, rhodium/active carbon and palladium/active carbon are particularly more preferable. These catalysts can be used alone or in combination. In the case of using a catalyst in which a metal is loaded onto a support, the loaded amount is 0.1–50 wt %, preferably 0.5–30 wt %, and particularly more preferably 1–20 wt %. In addition, in order to enhance safety during handling or to prevent oxidation of the metal surface, a combination with water, mineral oil or the like can be used.

The transition metal complex may be in an amount of 0.0001–50 wt %, preferably 0.005–30 wt %, more preferably 0.01–20 wt %, based on the total weight of the salt (product) of the step (c).

The hydrogenolysis of the step (d) may be conducted by using hydrogen in an amount of at least one mole, per mol of the salt obtained by the step (c). It is, however, usual to use hydrogen excessively due to the hydrogenolysis under a hydrogen atmosphere. The hydrogen pressure may be 0.01–10 MPa, preferably 0.05–5 MPa, more preferably 0.1–2 MPa.

The source of hydrogen for conducting the step (d) may be formic acid, ammonium formate, hydrazine or the like, as well as molecular hydrogen.

The reaction solvent of the step (d) can be selected from (1) aliphatic hydrocarbons such as n-pentane, n-hexane, c-hexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; (5) esters such as ethyl acetate and n-butyl acetate; (6) nitriles such as acetonitrile and propionitrile; (7) alcohols such as methanol, ethanol, n-propanol, and i-propanol; (8) carboxylic acids such as acetic acid, propionic acid, and butyric acid; (9) acidic aqueous solutions such as hydrochloric acid, sulfuric acid, hydrobromic acid, p-toluenesulfonic acid and 10-camphorsulfonic acid; and (10) water. Among these, toluene, ethyl acetate, methanol, ethanol, i-propanol, acetic acid and hydrochloric acid aqueous solution are preferable, while methanol, ethanol, i-propanol and hydrochloric acid aqueous solution are particularly more preferable. These reaction solvents can be used alone or in combination.

The hydrogenolysis of the step (d) may be conducted at a temperature of −50 to +160° C., preferably −25 to +120° C., more preferably 0 to +10° C.

It is possible to obtain a crude product of the step (d) by conducting an ordinary post-treatment after the reaction. According to need, the crude product can be subjected to a purification such as the use of activated carbon, distillation, recrystallization, or column chromatography, thereby obtaining a phthalate of or benzenesulfonate of optically active (R)-1-(4-trifluoromethylphenyl)ethylamine, which is represented by the formula [6] or [7], with high purity.

Optically active (R)-1-(4-trifluoromethylphenyl)ethylamine of the formula [1] (see the above reaction scheme) can efficiently be recovered by neutralization of the step (e), as explained in the following.

The neutralization of the step (e) can be conducted by using an inorganic base aqueous solution, followed by extraction with an organic solvent to recover the target product of the process.

The step (e) can be conducted under an inert gas atmosphere. The inert gas may be nitrogen or argon.

The inorganic base used in the step (e) can be selected from sodium hydroxide, sodium carbonate, sodium hydrogencarbonate, potassium hydroxide, potassium carbonate, and potassium hydrogencarbonate. Of these, sodium hydroxide and potassium hydroxide are preferable, while sodium hydroxide is more preferable.

The concentration of the inorganic base aqueous solution is not particularly limited as long as the resulting optically active (R)-1-(4-trifluoromethylphenyl)ethylamine is not decomposed in the solution. Its concentration can suitably be selected in view of solubility of the inorganic base in water and is preferably 1–50 wt %, more preferably 1–30 wt %.

The inorganic base aqueous solution may be added in an amount such that the aqueous layer is made to be basic. It is preferable to use the inorganic base aqueous solution excessively in order to improve the extraction efficiency.

The extraction solvent for extracting optically active (R)-1-(4-trifluoromethylphenyl)ethylamine can be selected from (1) aliphatic hydrocarbons such as n-pentane, n-hexane, c-hexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; and (5) esters such as ethyl acetate and n-butyl acetate. Of these, toluene, t-butyl methyl ether and ethyl acetate are preferable, while toluene and ethyl acetate are more preferable. These solvents can be used alone or in combination.

The temperature for conducting the step (e) is not particularly limited, as long as optically active (R)-1-(4-trifluoromethylphenyl)ethylamine is not decomposed. It is preferably 0–50° C., more preferably 0–30° C.

After the extraction, the resulting organic layer is concentrated to dryness, thereby obtaining a crude product of optically active (R)-1-(4-trifluoromethylphenyl)ethylamine. According to need, this crude product can be subjected to a purification such as the use of activated carbon, distillation, recrystallization, or column chromatography, thereby obtaining optically active (R)1-(4-trifluoromethylphenyl)ethylamine with high purity.

The following nonlimitative examples are illustrative of the present invention. Hereinafter, with respect to the products of the step (b), an isomer in which a newly-formed asymmetric carbon has R configuration is referred to as "R-R isomer", and another isomer in which a newly-formed asymmetric carbon has S configuration is referred to as "S-R isomer".

EXAMPLE 1

Step (a) (Dehydrocondensation)

At first, 94.92 g (504.89 mmol, 1.00 equivalent) of 4'-(trifluoromethyl)acetophenone, 67.20 g (555.37 mmol, 1.10 equivalents) of (R)-1-phenylethylamine, and 3.43 g (25.22 mmol, 0.05 equivalents) of zinc chloride were dissolved in 700 ml of toluene. The resulting solution was heated under reflux for 13.4 hr, while water (by-product) was removed from a Dean-Stark trap. The resulting reaction liquid was washed one time with 300 ml of 5% sodium hydroxide aqueous solution and three times with 300 ml of 1.5N ammonium chloride aqueous solution. The recovered organic layer was concentrated to dryness, thereby obtaining 155.56 g of a crude product of an optically active imine of the following formula [10]. Conversion was found by gas chromatography to be 99% or higher. This crude product was subjected to the following asymmetric reduction of Example 2 without conducting purification.

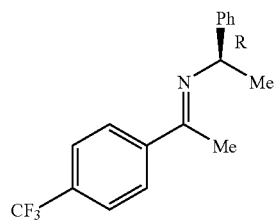

[10]

$^1$H-NMR (TMS, CDCl$_3$): 1.54 (d, 6.6 Hz, 3H), 2.29 (s, 3H), 4.85 (q, 6.6 Hz, 1H), 7.24 (t, 7.6 Hz, 1H), 7.34 (t, 7.6 Hz, 2H), 7.46 (d, 7.6 Hz, 2H), 7.63 (d, 8.3 Hz, 2H), and 7.94 (d, 8.3 Hz, 2H).

EXAMPLE 2

Step (b) (Asymmetric Reduction)

At first, 155.56 g (504.89 mmol, 1.00 equivalent) of the optically active imine of the formula [10] obtained by Example 1 were dissolved in 505 ml of methanol. The resulting solution was cooled down to 0° C. Then, 19.19 g (605.00 mmol, 1.00 equivalent) of sodium borohydride were added by spending 1 hr, and stirring was conducted for 1.5 hr at the same temperature. Then, 200 ml of 1N hydrochloric acid aqueous solution were added to the reaction liquid to terminate the reaction. Then, the reaction liquid was made basic with 300 ml of 3N sodium hydroxide aqueous solution. The reaction liquid was extracted three times with 300 ml of toluene, followed by washing one time with 200 ml of saturated brine. The collected organic layer was concentrated to dryness, thereby obtaining 158.69 g of a crude product of the optically active secondary amine of the formula [3]. It was found by gas chromatography that conversion of the crude product was at least 99% and that the ratio of a diastereomer of R-R configuration to a diastereomer of S-R configuration was 85:15. This crude product was subjected to the reaction of Example 3 without conducting purification.

The NMR data of the crude product are as follows. $^1$H-NMR (TMS, CDCl$_3$) of R-R configuration: 1.27 (d, 6.6 Hz, 3H), 1.29 (d, 6.6 Hz, 3H), 1.59 (br, 1H), 3.45 (q, 6.6 Hz, 1H), 8.57 (q, 6.6 Hz, 1H), and 7.12–7.67 (m, 9H). $^1$H-NMR (TMS, CDCl$_3$) of S-R configuration: 1.37 (d, 6.8 Hz, 6H), 1.59 (br, 1H), 3.76 (q, 6.8 Hz, 1H), 3.84 (q, 6.8 Hz, 1H), and 7.12–7.67 (m, 9H).

EXAMPLE 3

Step (c) (Phthalate Formation and Its Recrystallization)

To 518 ml of i-propanol, 158.69 g (504.89 mmol, 1.00 equivalent) of the crude product of the optically active secondary amine obtained in Example 2, 83.81 g (504.88 mmol, 1.00 equivalent) of phthalic acid and 740 ml of n-heptane were added, followed by stirring for 1 hr at 70° C. The reaction mixture was further stirred for 12 hr, while it was allowed to cool down gradually to room temperature. The precipitated crystals were filtered, washed with 100 ml of n-heptane, and vacuum-dried, thereby obtaining 187.89 g of crystals of a phthalate of the optically active secondary amine, which is represented by the formula [4]. The diastereomer excess ratio of the crystals was determined by gas chromatography in a manner that the phthalate was turned into a free base with 1N sodium hydroxide aqueous solution. The result was 97.9% de.

The obtained phthalate was recrystallized as follows, The total amount of the obtained crystals (phthalate) was added to 900 ml of i-propanol and then dissolved therein under heating. The reaction liquid was stirred for 12 hr while it was allowed to cool down gradually to room temperature. The precipitated crystals were filtered, washed with 100 ml of n-heptane, and vacuum dried, thereby obtaining 170.21 g of crystals of a phthalate of the optically active secondary amine, which is represented by the formula [4]. The diastereomer excess ratio of the crystals was determined as above. The result was 100% de, The total yield from Example 1 to Example 3 was 73%.

The NMR data of the phthalate are as follows. $^1$H-NMR (TMS, CDCl$_3$): 1.80 (d, 6.8 Hz, 6H), 4.04 (q, 6.8 Hz, 1H), 4.13 (q, 6.8 Hz, 1H), 7.35–7.73 (m, 11H), 8.45–8.55 (m, 2H), and 10.60 (br, 3H).

EXAMPLE 4

Step (d) (Phthalate Hydrogenolysis)

To 32 ml of methanol, 14.81 g (82.27 mmol) of the recrystallized phthalate (having 100% de) of the optically active secondary amine obtained in Example 3 and 158 mg (0.03 wt %) of a palladium catalyst (having 5% palladium carried on an activated carbon containing 50 wt % of water) were added. The reaction mixture was stirred at 60° C. for 12.3 hr, while the hydrogen pressure was adjusted to 0.5 MPa. Then, the reaction liquid was filtrated with CELITE (trade name), concentrated, and vacuum-dried, thereby obtaining of a crude product of a phthalate of the optically active (R)-1-(4-trifluoromethylphenyl)ethylamine, which is represented by the formula [6]. Conversion of the crude product was found by gas chromatography to be at least 99%.

The NMR data of the phthalate are as follows. $^1$H-NMR (TMS, CDCl$_3$): 1.59 (d, 6.6 Hz, 3H), 4.44 (q, 6.6 Hz, 1H), 7.40–7.60 (m, 6H), 7.90–8.10 (m, 2H), 9.42 (br, 4H).

EXAMPLE 5

Step (e) (Phthalate Neutralization)

At first, 50 ml of 3N sodium hydroxide aqueous solution were added to the total amount of the crude product of the phthalate of the optically active (R)-1-(4-trifluoromethylphenyl)ethylamine to make it basic. The reaction mixture was extracted three times with 100 ml of ethyl acetate. The resulting organic layer was washed one time with 100 ml of saturated brine, concentrated, and vacuum-dried, thereby obtaining a crude product of the optically active (R)-1-(4-trifluoromethylphenyl)ethylamine represented by the formula [1]. The crude product was purified by distillation, thereby obtaining 4.90 g of a purified product (boiling point: 73–74° C. under 9 mmHg). The purified product was found to have a chemical purity of 99.5% and an enantiomeric excess ratio of 100% ee. The total yield from Example 4 to Example 5 was 80%.

The NMR data of the optically active (R)-1-(4-trifluoromethylphenyl)ethylamine are as follows.

$^1$H-NMR (TMS, CDCl$_3$): 1.40 (d, 6.8 Hz, 3H), 1.60 (br, 2H), 4.19 (q, 6.8 Hz, 1H), 7.46 (d, 8.2 Hz, 2H), and 7.59 (d, 8.2 Hz, 2H).

EXAMPLE 6

Step (c) (Benzensulfonate Formation and Its Recrystallization)

At first, 151.55 g (504.89 mmol, 1.00 equivalent) of a crude product of the optically active secondary amine of the formula [3] were obtained by repeating Examples 1 and 2. This crude product was found by gas chromatography to have a ratio of a diastereomer of R-R configuration to a diastereomer of S-R configuration of 84:16. To 518 ml of i-propanol, the total amount (151.55 g) of the crude product and 88.86 g (504.89 mmol, 1.00 equivalent) benzenesulfonic acid monohydrate and 740 ml of n-heptane were added, followed by stirring for 1 hr at 70° C. The reaction mixture was further stirred for 12 hr, while it was allowed to cool down gradually to room temperature. The precipitated crystals were filtered, washed with 100 ml of n-heptane, and vacuum-dried, thereby obtaining 182.16 g of crystals of a benzenesulfonate of the optically active secondary amine, which is represented by the formula [5]. The diastereomer excess ratio of the crystals was determined by gas chromatography in a manner that the benzenesulfonate was turned into a free base with 1N sodium hydroxide aqueous solution. The result was 97.6% de.

The obtained benzenesulfonate was recrystallized as follows. The total amount of the obtained crystals (benzenesulfonate) was added to 856 ml of i-propanol and then dissolved therein under heating. The reaction liquid was stirred for 12 hr while it was allowed to cool down gradually to room temperature. The precipitated crystals were filtered, washed with 100 ml of n-heptane, and vacuum-dried, thereby obtaining 163.95 g of crystals of a benzenesulfonate of the optically active secondary amine, which is represented by the formula [5]. The diastereomer excess ratio of the crystals was determined as above. The result was 99.7% de. The total yield of the recrystallized benzenesulfonate from 4'-(trifluoromethyl)acetophenone was 72%.

The NMR data of the benzenesulfonate are as follows.

$^1$H-NMR (TMS, CDCl$_3$): 1.84 (d, 5.6 Hz, 6H), 3.84 (q, 5.6 Hz, 1H), 3.95 (q, 5.6 Hz, 1H), 7.20–7.60 (m, 12H), 8.03–8.17 (m, 2H), and 9.73 (br, 2H).

EXAMPLE 7

Step (d) (Benzenesulfonate Hydrogenolysis)

To 22 ml of methanol, 9.83 g (21.80 mmol) of the recrystallized benzenesulfonate (having 99.7% de) of the optically active secondary amine obtained in Example 6 and 138 mg (0.04 wt %) of a palladium catalyst (having 5% palladium carried on an activated carbon containing 50 wt % of water) were added. The reaction mixture was stirred at 60° C. for 13.6 hr, while the hydrogen pressure was adjusted to 0.5 MPa. Then, the reaction liquid was filtrated with CELITE (trade name), concentrated, and vacuum-dried, thereby obtaining of a crude product of a benzenesulfonate of the optically active (R)-1-(4-trifluoromethylphenyl)ethylamine, which is represented by the formula [7]. Conversion of the crude product was found by gas chromatography to be at least 99%.

The NMR data of the benzenesulfonate are as follows.

$^1$H-NMR (TMS, CD$_3$OD): 1.64 (d, 6.8 Hz, 3H), 4.56 (q, 6.8 Hz, 1H), 7.38–7.48 (m, 3H), 7.65 (d, 8.5 Hz, 2H), 7.73 (d, 8.5 Hz, 2H), and 7.78–7.85 (m, 2H).

EXAMPLE 8

Step (e) (Benzenesulfonate Neutralization)

At first, 30 ml of 3N sodium hydroxide aqueous solution were added to the total amount of the crude product of the benzenesulfonate of the optically active (R)-1 (4-trifluoromethylphenyl)ethylamine, which had been obtained in Example 7, to make it basic. The reaction product was extracted three times with 60 ml of ethyl acetate. The resulting organic layer was washed one time with 60 ml of saturated brine, concentrated, and vacuum-dried, thereby obtaining a crude product of the optically active (R)-1-(4-trifluoromethylphenyl)ethylamine represented by the formula [1]. The crude product was purified by distillation, thereby obtaining 3.17 g of a purified product (boiling point: 73–74° C. under 9 mmHg). The purified product was found to have a chemical purity of 99.4% and an enantiomeric excess ratio of 99.7% ee. The total yield of the optically active (R)-1-(4-trifluoromethylphenyl)ethylamine from 4'-(trifluoromethyl)acetophenone was 77%.

The NMR data of the optically active (R)-1-(4-trifluoromethylphenyl)ethylamine were identical with those of Example 5

The entire disclosure of Japanese Patent Application No. 2002-146983 filed on May 21, 2002, including specification, claims and summary, is incorporated herein by reference in its entirety.

What is claimed is:

1. A process for producing optically active (R)-1-(4-trifluoromethylphenyl)ethylamine represented by the formula [1], the process comprising the steps of:
   (a) reacting 4'-(trifluoromethyl)acetophenone represented by the formula [8], with optically active (R)-1-phenylethylamine represented by the formula [9] under an acidic condition to generate a dehydrocondensation, thereby obtaining an optically active imine represented by the formula [2];
   (b) asymmetrically reducing the optically active imine into an optically active secondary amine represented by the formula [3];
   (c) reacting the optically active secondary amine with an organic acid that is phthalic acid or benzenesulfonic acid, thereby obtaining a product that is a phthalate of the optically active secondary amine or a benzenesulfonate of the optically active secondary amine, the phthalate and the benzenesulfonate being respectively represented by the formulas [4] and [5];
   (d) subjecting the product of the step (c) to a hydrogenolysis, thereby obtaining a product that is a phthalate of optically active (R)-1-(4-trifluoromethylphenyl)ethylamine or a benzenesulfonate of optically active (R)-1-(4-trifluoromethylphenyl)ethylamine, the phthalate and the benzenesulfonate being respectively represented by the formulas [6] and [7]; and
   (e) neutralizing the product of the step (d) into the optically active (R)-1-(4-trifluoromethylphenyl)ethylamine

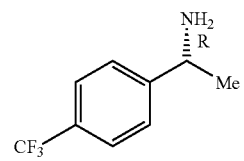

[1]

where a zigzag line in the formula [2] indicates that the optically active imine is in an E configuration or Z configuration,

[1]
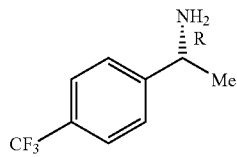

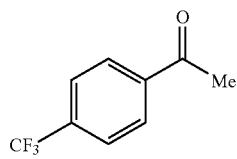

[9]
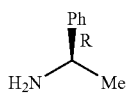

[2]
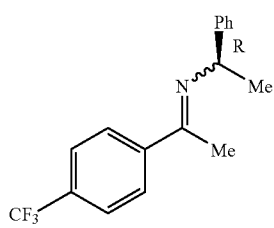

(4)
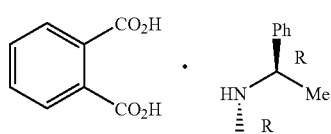

(5)
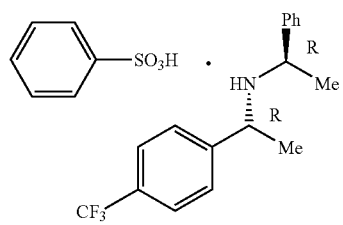

(6)
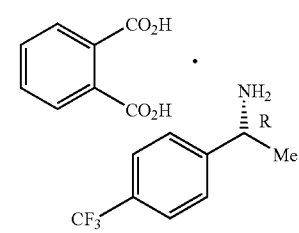

-continued (7)
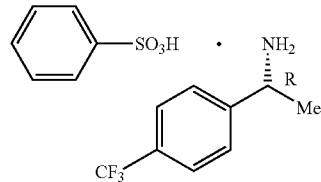

[8] where * represents an asymmetric carbon, and the optically active secondary amine comprises a first stereoisomer of R configuration and a second stereoisomer of S configuration, the first stereoisomer is in an amount greater than that of the second stereoisomer.

2. A process according to claim 1, wherein the step (a) is conducted in toluene as a reaction solvent, while water as a by-product of the step (a) is removed from a reaction system of the step (a).

3. A process according to claim 1, wherein the acidic condition of the step (a) is made by an acid catalyst that is p-toluenesulfonic acid or zinc chloride.

4. A process according to claim 1, wherein the step (b) is conducted by asymmetrically reducing the optically active imine by a hydride that is selected from the group consisting of $LiAlH_4$, diborane, $NaBH_4$, and $LiBH_4$.

5. A process according to claim 1, wherein the step (b) is conducted in a reaction solvent that is selected from the group consisting of diethyl ether, tetrahydrofuran, t-butyl methyl ether, methanol, ethanol, and i-propanol.

6. A process according to claim 1, wherein, prior to the step (d), the product of the step (c) is purified by recrystallization with a recrystallization solvent.

7. A process according to claim 6, wherein the recrystallization solvent is selected from the group consisting of n-hexane, n-heptane, toluene, methylene chloride, t-butyl methyl ether, acetone, ethyl acetate, acetonitrile, methanol, ethanol, n-propanol, and i-propanol.

8. A process according to claim 1, wherein the hydrogenolysis of the step (d) is conducted in the presence of a catalyst comprising a transition metal that is in a form of element or compound.

9. A process according to claim 8, wherein the transition metal is carried on an activated carbon as a carrier of the catalyst.

10. A process according to claim 1, wherein the hydrogenolysis of the step (d) is conducted in the presence of a reaction solvent that is selected from the group consisting of toluene, ethyl acetate, methanol, ethanol, i-propanol, acetic acid, and a hydrochloric acid aqueous solution.

11. A process according to claim 1, wherein the step (e) is conducted by neutralizing the product of the step (d) with sodium hydroxide.

12. A process for producing optically active (R)-1-(4-trifluoromethylphenyl)ethylamine represented by the formula [1],

[1]
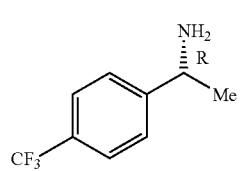

-continued

[6]
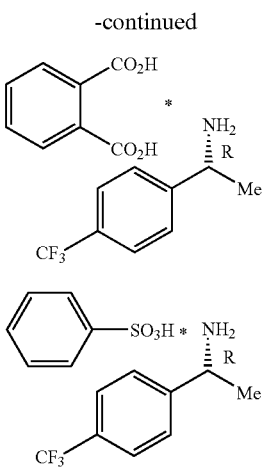

[7]
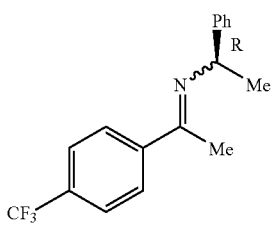

the process comprising the step of neutralizing an organic acid salt into the optically active (R)-1-(4-trifluoromethylphenyl)ethylamine, the organic acid salt being a phthalate of optically active (R)-1-(4-trifluoromethylphenyl)ethylamine or a benzenesulfonate of optically active (R)-1-(4-trifluoromethylphenyl)ethylamine, the phthalate and the benzenesulfonate being respectively represented by the formulas [6] and [7].

13. An optically active imine represented by the formula [2], which is an intermediate for producing optically active (R)-1-(4-trifluoromethylphenyl)ethylamine,

[2]
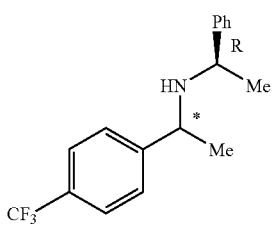

where a zigzag line in the formula [2] indicates that the optically active imine is in an E configuration or Z configuration.

14. An optically active secondary amine represented by the formula [3], which is an intermediate for producing optically active (R)-1-(4-trifluoromethylphenyl)ethylamine,

[3]
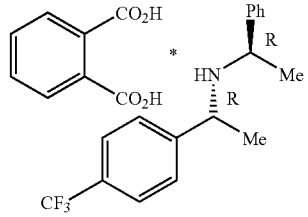

where * represents an asymmetric carbon, and the optically active secondary amine comprises a first stereoisomer of R configuration and a second stereoisomer of S configuration, the first stereoisomer is in an amount greater than that of the second stereoisomer.

15. A phthalate of an optically active secondary amine, the phthalate being an intermediate for producing optically active (R)-1-(4-trifluoromethylphenyl)ethylamine.

[4]
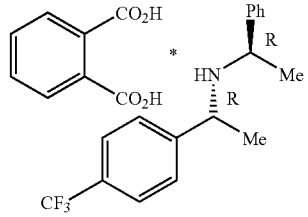

and being represented by the formula [4].

16. A benzenesulfonate of an optically active secondary amine, the benzenesulfonate being an intermediate for producing optically active (R)-1-(4-trifluoromethylphenyl)ethylamine.

[5]
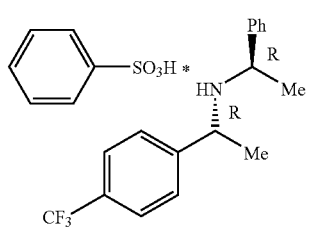

and being represented by the formula [5].

17. A phthalate of optically active (R)-1-(4-trifluoromethylphenyl)ethylamine.

[6]
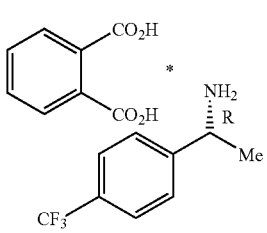

the phthalate being represented by the formula [6].

18. A benzenesulfonate of optically active (R)-1-(4-trifluoromethylphenyl)ethylamine.

[7]
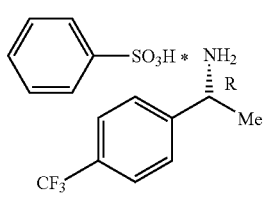

the benzenesulfonate being& represented by the formula [7].

* * * * *